US00PP25132P2

(12) United States Plant Patent
Verhoef

(10) Patent No.: US PP25,132 P2
(45) Date of Patent: Dec. 2, 2014

(54) ***WEIGELA* PLANT NAMED 'VERWEIG 6'**

(50) Latin Name: *Weigela florida*
Varietal Denomination: Verweig 6

(71) Applicant: Gijsbertus Verhoef, Hazerswoude (NL)

(72) Inventor: Gijsbertus Verhoef, Hazerswoude (NL)

( * ) Notice: Subject to any disclaimer, the term of this patent is extended or adjusted under 35 U.S.C. 154(b) by 128 days.

(21) Appl. No.: 13/694,554

(22) Filed: Dec. 12, 2012

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — C. A. Whealy

(57) ABSTRACT

A new and distinct cultivar of *Weigela* plant named 'Verweig 6', characterized by its upright and mounding plant habit; freely branching habit; bright green-colored leaves; freely flowering habit; remontant-flowering habit with plants flowering during the spring, summer and fall in The Netherlands; dark red-colored flowers; and good garden performance.

2 Drawing Sheets

Botanical designation: *Weigela florida*.
Cultivar denomination: 'VERWEIG 6'.

BACKGROUND OF THE INVENTION

The present invention relates to a new and distinct cultivar of *Weigela* plant, botanically known as *Weigela florida* and hereinafter referred to by the name 'Verweig 6'.

The new *Weigela* plant is a product of a planned breeding program conducted by the Inventor in Hazerswoude-Dorp, The Netherlands. The objective of the breeding program was to develop new freely and remontant-flowering *Weigela* plants with attractive leaf and flower colors.

The new *Weigela* plant originated from an open-pollination of *Weigela florida* 'Red Prince', not patented, as the female, or seed, parent with an unknown selection of *Weigela florida*, as the male, or pollen, parent. The new *Weigela* plant was discovered and selected by the Inventor as a single flowering plant from within the progeny of the stated open-pollination in a controlled environment in Hazerswoude-Dorp, The Netherlands.

Asexual reproduction of the new *Weigela* plant by softwood cuttings in Hazerswoude-Dorp, The Netherlands has shown that the unique features of this new *Weigela* plant are stable and reproduced true to type in successive generations of asexual reproduction.

SUMMARY OF THE INVENTION

Plants of the new *Weigela* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Verweig 6'. These characteristics in combination distinguish 'Verweig 6' as a new and distinct *Weigela* plant:

1. Upright and mounding plant habit.
2. Freely branching habit.
3. Bright green-colored leaves.

4. Freely flowering habit.
5. Remontant-flowering habit with plants flowering during the spring, summer and fall in The Netherlands.
6. Dark red-colored flowers.
7. Good garden performance.

In side-by-side comparisons conducted in Hazerswoude, The Netherlands, plants of the new *Weigela* differ primarily from plants of the female parent, 'Red Prince', in flowering habit as plants of 'Red Prince' flower only during the spring in The Netherlands.

Plants of the new *Weigela* can be compared to plants of the *Weigela florida* 'Polka', not patented. In side-by-side comparisons plants of the new *Weigela* differed primarily from plants of 'Polka' in the following characteristics:

1. Plants of the new *Weigela* and 'Polka' differed in flower color as plants of 'Polka' had pink-colored flowers.
2. Plants of the new *Weigela* had a remontant-flowering habit whereas plants of 'Polka' did not have a remontant-flowering habit.

BRIEF DESCRIPTION OF THE PHOTOGRAPHS

The accompanying colored photographs illustrate the overall appearance of the new *Weigela* plant showing the colors as true as it is reasonably possible to obtain in colored reproductions of this type. Colors in the photographs may differ slightly from the color values cited in the detailed botanical description which accurately describe the colors of the new *Weigela* plant.

The photograph on the first sheet comprises a side perspective view of a typical flowering plant of 'Verweig 6'.

The photograph on the second sheet is a close-up view of a typical flowering stem of 'Verweig 6'.

DETAILED BOTANICAL DESCRIPTION

The aforementioned photographs, following observations and measurements describe plants grown during the summer in one-gallon containers in an outdoor nursery in Grand Haven, Mich. and under cultural practices typical of commercial production. Plants were one year old when the photographs and description were taken. In the following description, color references are made to The Royal Horticultural Society Colour Chart, 2001 Edition, except where general terms of ordinary dictionary significance are used.

Botanical classification: *Weigela florida* 'Verweig 6'.

Parentage:

*Female or seed, parent.*—*Weigela florida* 'Red Prince', not patented.

*Male or pollen, parent.*—Unknown selection of *Weigela florida*, not patented.

Propagation:

*Type.*—By softwood cuttings.

*Time to initiate roots, summer.*—About 20 days at temperatures of 20° C.

*Time to produce a rooted young plant, summer.*—About three months at temperatures of 20° C.

*Root description.*—Fine to thick, fibrous.

*Rooting habit.*—Freely branching; dense.

Plant description:

*Plant and growth habit.*—Perennial shrub; upright and mounding plant habit; rapid growth rate; vigorous growth habit.

*Branching habit.*—Freely branching habit with numerous lateral branches developing per plant; pinching enhances lateral branch development; dense and bushy plant form.

*Plant height.*—About 130 cm.

*Plant diameter.*—About 120 cm.

Lateral branch description:

*Length.*—About 50 cm.

*Diameter.*—About 5 mm.

*Internode length.*—About 5 cm.

*Texture.*—Smooth, glabrous.

*Color, developing.*—Close to 145A.

*Color, fully developed.*—Close to 197D.

Foliage description:

*Arrangement.*—Opposite; simple.

*Length.*—About 10 cm.

*Width.*—About 3.5 cm.

*Shape.*—Elliptic.

*Apex.*—Narrowly acute.

*Base.*—Attenuate, tapering.

*Margin.*—Serrulate, undulate.

*Texture, upper and lower surfaces.*—Smooth, glabrous.

*Venation pattern.*—Pinnate.

*Color.*—Developing leaves, upper and lower surfaces: Close to 143C tinged with close to 180B. Fully expanded leaves, upper surface: Close to 146A; venation, close to 142B. Fully expanded leaves, lower surface: Close to 143C; venation, close to 142B.

*Petiole.*—Length: About 2 mm. Diameter: About 3 mm to 4 mm. Texture, upper and lower surfaces: Smooth, glabrous. Color, upper and lower surfaces: Close to 142A.

Flower description:

*Flower arrangement and habit.*—Salverform flowers arranged in terminal and upper axillary clusters; typically 10 to 20 flowers development per lateral branch; flowers face mostly upright to outwardly.

*Fragrance.*—None detected.

*Natural flowering season.*—Plants of the new *Weigela* have a remontant-flowering habit and flower repeatedly from May, and throughout the summer to October in Grand Haven, Mich.

*Flower longevity.*—Flowers last about six weeks on the plant; flowers not persistent.

*Flower diameter.*—About 1.5 cm.

*Flower length* (*height*).—About 4 cm.

*Flower buds.*—Length: About 1 cm. Diameter: About 5 mm. Shape: Oblanceolate. Color: Close to 187A.

*Corolla.*—Arrangement: Salverform; five petals fused into a tube with separate petal lobes. Petal lobe length: About 1 cm. Petal lobe width: About 1.1 cm. Petal lobe shape: Roughly spatulate. Petal lobe apex: Obtuse. Petal lobe margin: Entire. Petal texture, upper and lower surfaces: Smooth, glabrous. Color: When opening, upper and lower surfaces: Close to 53A. Fully opened, upper and lower surfaces: Close to 53A; color does not fade with development.

*Sepals.*—Quantity per flower: Five in a single whorl, fused; campanulate calyx. Length: About 5 mm. Width: About 1 mm. Shape: Lanceolate. Apex: Narrowly acute. Margin: Entire. Sepal texture, upper and lower surfaces: Smooth; glabrous. Color, upper and lower surfaces: Close to 53B.

*Peduncles.*—Length: About 1 cm. Diameter: About 1 mm. Strength: Strong; flexible. Texture: Smooth, glabrous. Color: Close to 143B.

*Reproductive organs.*—Stamens: Quantity and arrangement: Five per flower. Anther shape: Narrowly oblong. Anther size: About 1 mm by 2 mm. Anther color: Close to 155D. Pollen amount: Scarce. Pistils: Quantity: One per flower. Pistil length: About 3.5 cm. Style length: About 3.4 cm. Style color: Close to 155D. Stigma color: Close to 155D. Ovary color: Close to 144D. Seeds: Length: Less than 0.1 mm. Diameter: Less than 0.1 mm. Color: Brown.

Garden performance: Plants of the new *Weigela* have exhibited good tolerance to rain, wind and have been observed to tolerate temperatures from about −25° C. to about 33° C.

Pathogen & pest resistance: Plants of the new *Weigela* have not been observed to be resistant to pests and pathogens common to *Weigela* plants.

It is claimed:

1. A new and distinct *Weigela* plant named 'Verweig 6' as illustrated and described.

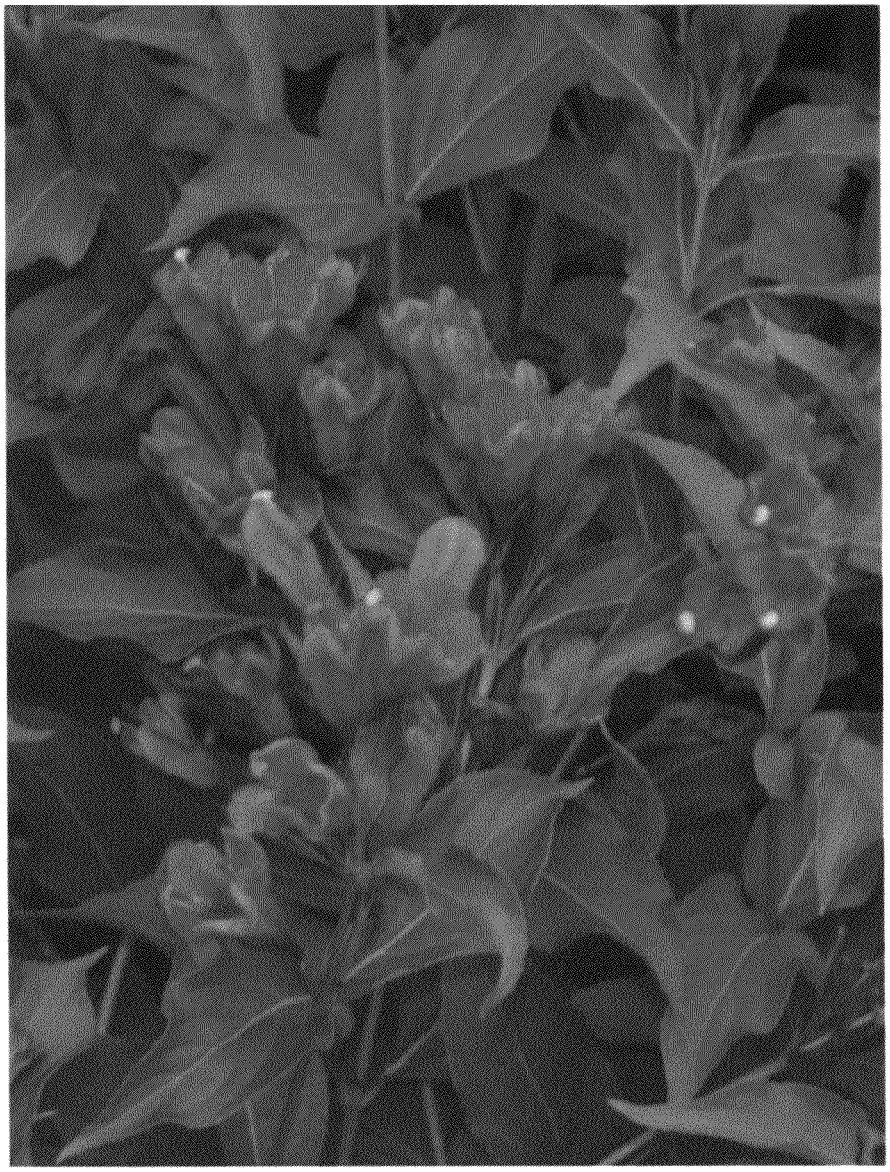

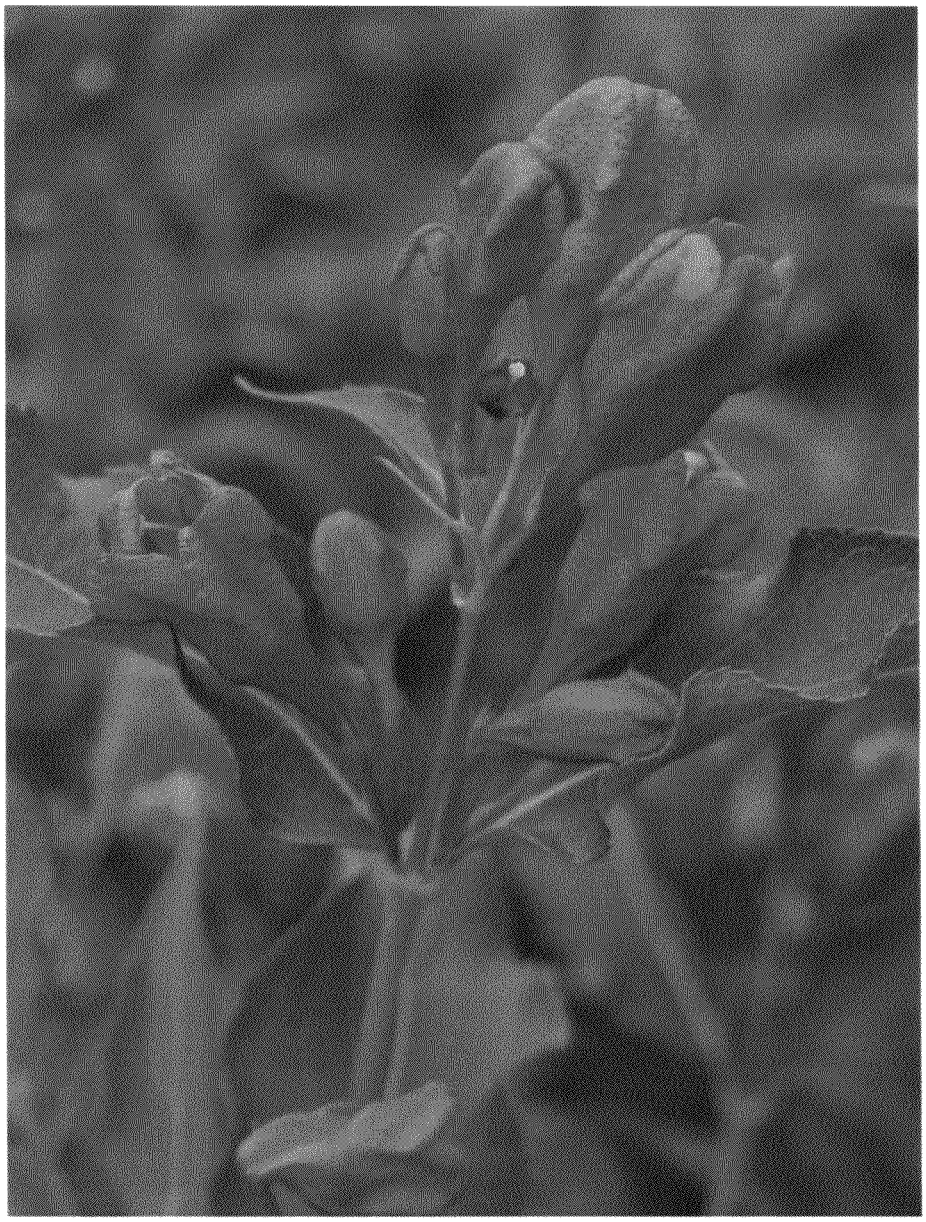

* * * * *